(12) United States Patent
Miller et al.

(10) Patent No.: US 10,881,055 B2
(45) Date of Patent: Jan. 5, 2021

(54) NUTRITIONALLY AND BOTANICALLY ENHANCED MYCELIAL MASS

(71) Applicant: GRV Fund, LLC, Jupiter, FL (US)

(72) Inventors: Andrew Hines Miller, Calistoga, CA (US); Jordan Seth Rubin, Koshkonong, MO (US)

(73) Assignee: BYO HOLDINGS, LLC, Koshkonong, MO (US)

( * ) Notice: Subject to any disclaimer, the term of this patent is extended or adjusted under 35 U.S.C. 154(b) by 0 days.

(21) Appl. No.: 16/265,164

(22) Filed: Feb. 1, 2019

(65) Prior Publication Data
US 2019/0320596 A1 Oct. 24, 2019

Related U.S. Application Data

(63) Continuation of application No. 14/680,269, filed on Apr. 7, 2015, now abandoned.

(60) Provisional application No. 61/983,244, filed on Apr. 23, 2014.

(51) Int. Cl.
*C12N 1/14* (2006.01)
*A01G 18/00* (2018.01)

(52) U.S. Cl.
CPC .............. *A01G 18/00* (2018.02); *C12N 1/14* (2013.01)

(58) Field of Classification Search
CPC . C05F 11/00; C05F 11/02; A01G 1/04; A01G 1/044; A01G 1/048
See application file for complete search history.

(56) References Cited

U.S. PATENT DOCUMENTS

| | | | | |
|---|---|---|---|---|
| 2,618,900 A * | 11/1952 | Humfeld | ............... | A01G 18/00 47/1.1 |
| 2,693,665 A * | 11/1954 | Humfeld | ............... | A01G 18/00 47/1.1 |
| 4,803,800 A * | 2/1989 | Romaine | ............... | A01G 18/00 47/1.1 |
| 5,086,800 A * | 2/1992 | Dunn | ............... | B60R 15/00 137/1 |
| 5,503,647 A * | 4/1996 | Dahlberg | ............... | C05D 9/00 47/1.1 |
| 6,061,957 A * | 5/2000 | Takashima | ............... | A01G 22/15 47/66.1 |
| 6,395,315 B1 * | 5/2002 | Matsuura | ............... | A21D 2/368 426/49 |
| 2004/0092014 A1 * | 5/2004 | Hiromoto | ............... | C05F 5/008 435/420 |
| 2004/0105869 A1 * | 6/2004 | Sakuma | ............... | A61K 36/07 424/195.15 |
| 2005/0178055 A1 * | 8/2005 | Miller | ............... | A01G 18/00 47/1.1 |
| 2007/0151020 A1 * | 7/2007 | Pondelick | ............... | B64D 11/02 4/665 |
| 2008/0160583 A1 * | 7/2008 | Wang | ............... | C12P 1/02 435/101 |
| 2013/0008215 A1 * | 1/2013 | Morikawa | ............... | A61K 33/26 71/23 |
| 2014/0302560 A1 * | 10/2014 | Kelly | ............... | C12N 1/14 435/71.1 |

FOREIGN PATENT DOCUMENTS

GB 1220807 A * 1/1971 ............. A01G 18/00

* cited by examiner

*Primary Examiner* — Magdalena Topolski
*Assistant Examiner* — Morgan T Barlow
(74) *Attorney, Agent, or Firm* — Barbara E. Johnson, Esq.

(57) ABSTRACT

The invention is an important innovation in mushroom culture in which not only are mycelia beneficially grown on the novel combination of a grain (or seed) and an herb, in the preferred embodiment of the invention the mycelial mass is grown in a co-fermentation with all of a grain (or seed), an herb and a juice.

4 Claims, No Drawings

NUTRITIONALLY AND BOTANICALLY ENHANCED MYCELIAL MASS

CROSS-REFERENCE TO RELATED APPLICATION

This patent application claims priority to, and incorporates herein by reference, U.S. Provisional patent application No. 61/983,244 filed 23 Apr. 2014. This application is more-a continuation of U.S. patent. Ser. No. 14/680,269 filed 7 Apr. 2015, also incorporated herein by reference.

BACKGROUND OF THE INVENTION

Field of the Invention

Improved fungiculture for edible and particularly medicinal mushrooms imparts better constituency and enhanced growth and strength of biomass and speed of fungiculture.

Description of Related Art

Traditional growth media for edible or medicinal mushrooms has conventionally included a variety of substrates, including but not limited to wood chips, sawdust, mulched straw (typically of wheat or rice); brewer's grain, stockyard, horse or poultry manure, ground corncobs, paper, coffee grounds, nut-, seed- and cocoa-bean-hulls, soybean, cottonseed or rice meal, or other generally chitinous substrates. One of the present inventors has previously grown mushrooms on particularly specified media, such as purple corn, to facilitate the uptake of desired nutrients in the mushroom end product. However, up until now, the engineering of mushroom mass as to a specialized constituency has been in its infancy. It simply has not been known, prior to this writing, what can be added to mushroom growth substrate that can be taken up in the mushroom mass and preserved into the mature, harvestable mushroom product. However, at this writing medicinal mushrooms are enjoying great popularity, due to their character as a robust natural substance which can be organically grown, safely maintained and shipped, and dried without loss of essential bioactive ingredients. Because edible and particularly medicinal mushrooms can transform into exceptional nutritional and pharmaceuticals of long shelf life and notable quality, a need remains for ways of growing mushroom biomass having desired composition and unusually hearty and fast growth characteristics.

SUMMARY OF THE INVENTION

In order to meet this need, the present invention is an innovative method of growing certain strains of mushrooms on newly specified media to create heretofore unattainable robust biomass having desired nutritional and pharmaceutical (nutraceutical) profiles. The fungi grown according to the invention are selected from the group consisting of: *Ganoderma lucidum; Ganoderma japonicum; Ganoderma applanatum; Ganoderma Tsugae; Lentinula edodes; Grifola frondosa; Tremella fuciformis; Tremella mesenterica; Cordyceps sinensis; Cordyceps militaris; Hericium erinaceus; Polyporus umbellatus; Schizophyllum commune; Fomes fomentarius; Inonotus obliquus; Lepiota procera; Auricularia auricula; Tuber melanosporum; Tricholoma matsutake; Hericium coralloides; Trametes versicolor; Phellinus linteus; Poria cocos; Antrodia camphorate; Flammulina velutipes; Pleurotus ostreatus; Pleurotus eryngii;* and *Agaricus blazei*. According to the invention, these fungus varieties are grown on media selected from the group consisting of (or preponderantly containing one or more of) Black rice; Ashwaghandha; Cacao nibs; Black Chia seed; Flax seed; Black Quinoa; Black Sesame; Hemp Seed; a leaf or flower of *Cannabis sativa*; a leaf or flower of *Cannabis indica*; Sunflower seeds; Pumpkin seeds; Spirulina; Lemon Peel; Chili Pepper; Kelp; Alfalfa leaf; Watercress; Cilantro; Sage; Thyme; Parsley; Broccoli Seed; Mate; green Coffee Beans; Roasted Coffee Beans; Green Tea; Rhodiola; Siberian Ginseng; Sea Buckthorn Berry; Black Soy Bean; Olive leaf; Cabbage; Milk Thistle seed; Milk Thistle leaf; Turmeric; Bupleurum; Artichoke leaf; Dandelion leaf; Dandelion root; Hibiscus flower; Ginkgo leaf; Bacopa; Periwinkle; Fava Bean; Peppermint; Hawthorn Berry; Cardamon; Garlic; Mung Bean; Astragalus Root; *Echinacea purpurea* root; *Echinacea augustifolia* root; *Echinacea augustifolia* leaf; Elder berries; Elder Flower; Goldenseal Leaf; Goldenseal root; Olive Leaf; Ginger; Orange Peel and Blossom; Clove; Cinnamon; Fennel; Kelp; Bergamot; Hibiscus Flower; Frankincense tears; Holy Basil; Celery seed; Bilberry leaf; *Gymnema sylvestre* leaf; Fenugreek; Bitter Melon; Saw Palmetto; Nettle; Red Clover Blossom; Black Cohosh; Chaste Tree Berries; Dong Quai Root; Hop Flowers; Licorice root; Wild Yam; Thyme Leaf; Oregano; Hyssop; Marjoram; American Ginseng; Red Panax Ginseng; White Panax Ginseng; Cruciferous vegetables; Schizandra; Goji Berry; Tribulus; Velvet Bean; Cranberry; Almonds; white Quinoa and Epimedium. The growth of the listed fungi on the listed medium gives new and unexpected results not only in mushroom constituency but in strength and viability of mushroom mass and faster and more robust growth than the same fungi can achieve on traditional growth substrates. More particularly, the invention in its preferred embodiment includes all of a fungal species, a juice, a grain and a seed—in a fermentation with all constituents together—in order to enhance the nutritional profile of the resulting product.

DETAILED DESCRIPTION OF THE INVENTION

The present invention comprises growing certain edible or medicinal mushrooms on specialized substrates (media) in the nature of HERBS, SPICES, FRUITS, VEGETABLES, ALGAE, GRAINS AND SEEDS. As described above, the present invention is an innovative method of growing certain strains of mushrooms on newly specialized media to create heretofore unattainable robust biomass having desired nutritional and pharmaceutical (nutraceutical) composition. The fungi grown according to the invention are selected from the group consisting of: *Ganoderma lucidum; Ganoderma japonicum; Ganoderma applanatum; Ganoderma Tsugae; Lentinula edodes; Grifola frondosa; Tremella fuciformis; Tremella mesenterica; Cordyceps sinensis; Cordyceps militaris; Hericium erinaceus; Polyporus umbellatus; Schizophyllum commune; Fomes fomentarius; Inonotus obliquus; Lepiota procera; Auricularia auricula; Tuber melanosporum; Tricholoma matsutake; Hericium coralloides; Trametes versicolor; Phellinus linteus; Poria cocos; Antrodia camphorate; Flammulina velutipes; Pleurotus ostreatus; Pleurotus eryngii;* and *Agaricus blazei*. According to the invention, these fungi varieties are grown on media selected from the group consisting of (or preponderantly containing one or more of) Black rice; Ashwaghandha; Cacao nibs; Black Chia seed; Flax seed; Black Quinoa; Black Sesame; Hemp Seed; leaf or flower of *Cannabis sativa*; leaf or flower of *Cannabis indica*; Sunflower seeds; Pumpkin seeds; Spirulina; Lemon Peel; Chili Pepper; Kelp; Alfalfa leaf; Watercress; Cilantro; Sage; Thyme; Parsley; Broccoli Seed; Mate; green Coffee Beans; Roasted Coffee Beans; Green Tea; Rhodiola; Siberian Ginseng; Sea Buckthorn Berry; Black Soy Bean; Olive leaf; Cabbage; Milk Thistle seed; Milk Thistle leaf; Turmeric; Bupleurum; Artichoke leaf; Dandelion leaf; Dandelion root; Hibiscus flower; Ginkgo leaf; Bacopa; Periwinkle; Fava Bean; Peppermint; Hawthorn Berry; Cardamon; Garlic; Mung Bean; Astragalus Root; *Echinacea purpurea* root; *Echinacea augustifolia* root; *Echinacea augustifolia* leaf; Elder berries; Elder Flower; Goldenseal Leaf; Goldenseal root; Olive Leaf; Ginger; Orange Peel and Blossom; Clove; Cinnamon; Fennel; Kelp; Bergamot; Hibiscus Flower; Frankincense tears; Holy Basil; Celery seed; Bilberry leaf; *Gymnema sylvestre* leaf; Fenugreek; Bitter Melon; Saw Palmetto; Nettle; Red Clover Blossom; Black Cohosh; Chaste Tree Berries; Dong Quai Root; Hop Flowers; Licorice root; Wild Yam; Thyme Leaf; Oregano; Hyssop; Marjoram; American Ginseng; Panax Ginseng—red and white; Cruciferous vegetables; Schizandra; Goji Berry; Tribulus; Velvet Bean; Cranberry; Almonds; white Quinoa and Epimedium. The growth of the listed fungi on the listed medium gives new and unexpected results not only in mushroom constituency but in strength and viability of mushroom mass and faster and more robust growth than the same fungi can achieve on traditional growth substrates.

Certified organic biologically active nutraceutical raw material compounds are produced by inoculating herbs, spices, fruits, teas, vegetables, algae, grains, seeds and dairy products with a range of cultures of functional fungi species' (symbiotic transformation system). The living cultures pre-digest the foods and herbs transforming and potentiating these ingredients. Grains and seeds are sprouted/germinated prior to inoculation. The STS (Symbiotic Transformation System) uses organic whole food ingredients, with zero filler ingredients, zero inactive ingredients, no isolated chemicals, no extracts resulting in a full spectrum potentiation of organic food factors. No sugars are used as culture stimulants. A unique lipid delivery system is contained within each formulation. Products created using the STS can be vegetarian/vegan friendly. Ingredients are not mixed together, they're fused together by a natural live fermentation process. Raw materials derived from this process are truly whole, truly live. The culture is never killed/terminated with enzymes or heat, that is, materials are truly raw, and dried only below 118 degrees F. These nutrient rich raw materials are grown using organic juices, milks and purees in addition to the base media. In the preferred embodiments of the invention, during the cultivation/fermentation process specific music is played providing frequency generating vibrations to impart energy into the finished products. The STS process creates whole foods rich in vitamins, amino acids, trace minerals, polysaccharides, Beta Glucans, Alpha Glucans, Proteoglycans, Antioxidants, Enzymes, Pectins, Ribonucleases, Ubiquitin like proteins, Arabinoxylines, coenzymes and chelated mineral activators may be added and greatly enhance the bioavailability of beneficial compounds taken up from the specified media.

The present media may be supplemented with liquid additions as follows. ORGANIC JUICES, MILKS, PUREES USED IN THIS INVENTION are listed below but not limited to: Organic Carrot Juice Concentrate; Organic Concord Grape Juice; Organic pomegranate Juice Concentrate; Organic Ginger Juice; Organic Blueberry Puree; Organic Acai Puree; Organic Plum Puree; Organic raspberry Puree; Organic Tomato Puree; Organic Cranberry Juice; Organic Goat Milk; Organic Heavy Cream; Organic Coconut Cream; Organic Coconut Water; Organic Cherry Juice; Organic Green Tea; Organic Apple Juice; Organic Vegetable Juice; Organic Pineapple Juice; Organic Aloe Juice; Organic cold brewed coffee; Organic Almond Milk; Organic Chicken Broth; Organic Vegetable Broth or Organic Roasted Coffee.

In the preferred embodiment of the invention, a fungal species is grown and fermented, both, with all of a grain (or seed), an herb and a juice, to give optimal medicinal and nutritional profiles to the resulting fungi. The inventors have determined that the co-fermentation of a juice, a seed (grain) and an herb, together with the fungi growth, distinctly enhances the mushroom composition compared to mushrooms grown on traditional inert media. Indeed—except for the applicant's prior patented "purple corn" mushroom growth medium (U.S. Pat. No. 7,178,285 entitled, "Functional substrates for growth of culinary and medicinal mushrooms") the industry has emphasized stable, inert and largely nutritionally irrelevant growth media for mushrooms. Now, however, the inventors realize that not only is the growth medium important for mushroom culture, that also there is a specific beneficial synergy that results when mushrooms are grown in a co-fermentation in which the growth media includes a grain (or seed), an herb and a juice, in additional to the mushroom mass or mycelial inoculant. Moreover, through experimentation, the inventors herein have determined even further that not all fungal species react the same to different specialized growth media. *Ophiocordyceps sinensis* and *Ophiocordyceps militaris* are the most sensitive of all the species tested, and require a particular combination of relatively higher fat seeds (one or more of black chia, sunflower, pumpkin, hemp, sesame or brown flax) and lower sugar juices (aloe vera, celery, parsley, cucumber) with one or more herbs, to give the best growth and the best mushroom composition. By contrast, other species (*Ganoderma lucidum, Trametes versicolor*, and *Hericium erinaceus*) have a wider tolerance to choice of growth media, meaning the juice does not need to be low sugar, but even these species grow better on relatively low fat seeds (red canihua, red quinoa, black quinoa, black/purple rice or purple millet) in combination with the juice and the herb, rather than on the higher fat seeds (see above). These beneficial combinations have already been quantified as follows. New and unexpectedly improved growth and mushroom composition result when certain ratios of inclusion of media constituents are observed. Across the mushroom species, these ratios are a constant: 20-25% of the seed or grain component, whether lower or higher fat, and 75-80% of the herb (botanical) such as Ashwaganda Root, Turmeric Rhizome, Milk Thistle Seed, Holy Basil Leaf, Ginger Rhizome; Oregano Leaf; Cinnamon Bark, Schizandra Berry, Amly Berry, Lemon Peel or Green Tea. Juices are not measured in percentages but instead are used in amounts that are sufficient for adequate hydration for the mushroom culture, and these amounts are within the skill of the art.

EXAMPLES OF PRODUCTS CREATED BY THIS INVENTION

*Cordyceps sinensis* cultivated/grown on Ashwaganda root—two adaptogenic compounds fused together through the technology of this invention. Rapid and dense growth of mycellium during the cultivation/fermentation process is noted. *Cordyceps* and Ashwaganda complement each other in their powerful medicinal qualities producing a tonic for health that is unique and exceptional. Furthermore, when

*Cordyceps sinensis* is grown on Ashwaganda root growth medium, growth is surprisingly fast and the biomass becomes robust at a speed that is unusual and unexpected.

*Hericium erinaceus* cultivated/grown on Ginkgo biloba leaves—this marriage of two prized nutritional ingredients that have been extensively researched for their Cognitive enhancing properties have been hailed for its potential application in slowing down the progression of mental decline and age related neuro degeneration. Rapid and dense growth of mycellium during the cultivation/fermentation process is noted.

*Cordyceps sinensis* is cultivated/grown on Cacao nibs to produce a nutritionally significant nutraceutical, confection ingredient and/or powder for protein and meal replacement products. Rapid and dense growth of mycelium during the cultivation/fermentation process is noted.

High Energy Whole Food Protein Powder consisting of Pumpkin Seed, Sunflower seed, Chia Seed, Hemp seed, Flax seed, Black sesame seed and Cacao in a base of organic concord grape juice innoculated with *Cordyceps sinensis*. Rapid and dense growth of mycellium during the cultivation/fermentation process is noted.

In order to prepare a *Ganoderma lucidum* product take 20-25% biomass (260-340 g per 1,363 grams total material on a dry weight basis) of one or more the following grains and seeds (more grains than seeds): red canihua; red quinoa; black quinoa; black/purple rice; purple millet; black chia seed; sunflower seed; pumpkin seed; hemp seed; sesame seed and brown flax seed, together with 75-80% (1000-1, 100 g. per 1,363 g total material on a dry weight basis) of the following one or more herbs: Ashwagandha root; Turmeric rhizome; Milk Thistle seed; Holy Basil Leaf; Ginger Rhizome; Oregano Leaf; Cinnamon Bark; Schizandra berry; Amly berry; lemon peel and green tea, and moisten with 500-1,000 ml total liquid taken from one or more of aloe vera, inner leaf juice; purple carrot juice; grape juice; apple juice; pomegranate juice; beet juice; parsley juice; or cabbage juice. The resulting biomass grows significantly faster than on neutral media and water, and produces a greater number of larger fungal fruiting bodies containing more polysaccharides, vitamins, minerals, essential fatty acids, polyphenolic antioxidants and organic acids tha typical fungal mycelia using standard growth media. Interestingly, the resulting mushroom does not carry the taste of the herbs or juices; such a mushroom does not taste of mushroom or cabbage. However, the fermentation greatly enhances the nutritional constituents and growth speed of the mushroom culture.

In order to prepare an *Orphicordyceps sinensis* or *Orphiocordyceps militaris* product take 20-25% biomass (260-340 g per 1,363 grams total material on a dry weight basis) of one or more the following grains and seeds (more grains than seeds): red canihua; red quinoa; black quinoa; black/purple rice; purple millet; black chia seed; sunflower seed; pumpkin seed; hemp seed; sesame seed and brown flax seed BUT emphasize the higher fat/lower starch ones, namely, black chia seed, sunflower seed, pumpkin seed, hemp seed, sesame seed and brown flax seed, together with 75-80% (1000-1,100 g. per 1,363 g total material on a dry weight basis) of the following one or more herbs: Ashwagandha root; Turmeric rhizome; Milk Thistle seed; Holy Basil Leaf; Panax Ginseng; Rhodicia Rosea; Schizandra berry; Amly berry; lemon peel and green tea, and moisten with 500-1,000 ml total liquid taken from one or more of aloe vera, inner leaf juice; celery juice; parsley juice or cucumber juice (these are the relatively lower sugar juices). The resulting biomass grows significantly faster than on neutral media and water, and produces a greater number of larger fungal fruiting bodies containing more polysaccharides, vitamins, minerals, essential fatty acids, polyphenolic antioxidants and organic acids than typical fungal mycelia using standard growth media. Interestingly, the resulting mushroom does not carry the taste of the herbs or juices; such a mushroom does not taste of mushroom or cabbage. However, the fermentation greatly enhances the nutritional constituents and growth speed of the mushroom culture.

In order to prepare a *Trametes versicolor* product take 20-25% biomass (260-340 g per 1,363 grams total material on a dry weight basis) of one or more the following grains and seeds (more grains than seeds): red canihua; red quinoa; black quinoa; black/purple rice; purple millet; black chia seed; sunflower seed; pumpkin seed; hemp seed; sesame seed and brown flax seed, together with 75-80% (1000-1, 100 g. per 1,363 g total material on a dry weight basis) of the following one or more herbs: Ashwagandha root; Turmeric rhizome; Milk Thistle seed; Holy Basil Leaf; Ginger Rhizome; Oregano Leaf; Cinnamon Bark; Schizandra berry; Amly berry; lemon peel and green tea, and moisten with 500-1,000 ml total liquid taken from one or more of aloe vera, inner leaf juice; purple carrot juice; grape juice; apple juice; pomegranate juice; beet juice; parsley juice; or cabbage juice. The resulting biomass grows significantly faster than on neutral media and water, and produces a greater number of larger fungal fruiting bodies containing more polysaccharides, vitamins, minerals, essential fatty acids, polyphenolic antioxidants and organic acids than typical fungal mycelia using standard growth media.

In order to prepare a *Hericium erinaceus* product take 20-25% biomass (260-340 g per 1,363 grams total material on a dry weight basis) of one or more the following grains and seeds (more grains than seeds): red canihua; red quinoa; black quinoa; black/purple rice; purple millet; black chia seed; sunflower seed; pumpkin seed; hemp seed; sesame seed and brown flax seed, together with 75-80% (1000-1, 100 g. per 1,363 g total material on a dry weight basis) of the following one or more herbs: Ashwagandha root; Turmeric rhizome; Milk Thistle seed; Holy Basil Leaf; Ginkgo Leaf; Bacopa; Periwinkle; Oregano Leaf; Schizandra berry; Amly berry; and green tea, and moisten with 500-1,000 ml total liquid taken from one or more of blueberry juice; purple carrot juice; grape juice; pomegranate juice; beet juice and/or red cabbage juice. The resulting biomass grows significantly faster than on neutral media and water, and produces a greater number of larger fungal fruiting bodies containing more polysaccharides, vitamins, minerals, essential fatty acids, polyphenolic antioxidants and organic acids than typical fungal mycelia using standard growth media. Even when blueberry juice is used, the resulting mushroom product does not taste like blueberries. For this and all examples mushroom culture and fermentation of grains, seeds, herb and juices are conducted at temperatures and pressures, as well as hydration rates, typical for mushroom culture at this writing.

The invention claimed is:

1. A method for enhancing the mushroom constituency of edible or medicinal mushrooms consisting essentially of:
    growing at least one fungus selected from the group consisting of *Ganoderma lucidum, Ganoderma japonicum, Ganoderma applanatum, Ganoderma Tsugae, Lentinula edodes, Grifola frondosa, Tremella fuciformis, Tremella mesenterica, Cordyceps sinensis, Cordyceps militaris, Hericium erinaceus, Polyporus Polyporous umbellatus, Schizophyllum commune, Fomes fomentarius, Inonotus obliquus, Lepiota procera,*

*Auricularia auricula, Tuber melanosporum, Tricholoma matsutake, Hericium coralloides, Trametes versicolor, Phellinus linteus, Poria cocos, Antrodia camphorata, Flammulina velutipes, Pleurotus ostreatus, Pleurotus eryngii,* and *Agaricus blazei* on a growth medium consisting essentially of a grain or seed selected from the group consisting of black rice, ashwaghandha, cacao nib, black chia seed, flax seed, black quinoa, black sesame, and hemp seed, together with an herbal component selected from the group consisting of a leaf or flower of *Cannabis sativa*, a leaf or flower of *Cannabis indica*, sunflower seed, pumpkin seed, spirulina, lemon peel, chili pepper, kelp, alfalfa leaf, watercress, cilantro, sage, thyme, parsley, broccoli seed, mate, green coffee bean, roasted coffee bean, green tea, rhodiola, Siberian ginseng, sea buckthorn berry, black soy bean, olive leaf, cabbage, milk thistle seed, milk thistle leaf, turmeric, bupleurum, artichoke leaf, dandelion leaf, dandelion root, hibiscus flower, ginkgo leaf, bacopa, periwinkle, fava bean, peppermint, hawthorn berry, cardamom, garlic, mung bean, astragalus root, *Echinacea purpurea* root, echinacea augustifolia root, echinacea augustifolia leaf, elder berry, elder flower, goldenseal leaf, goldenseal root, ginger, orange peel, orange blossom, clove, cinnamon, fennel, bitter orange, bergamot, frankincense tears, holy basil, celery seed, bilberry leaf, gymnema sylvestre leaf, fenugreek, bitter melon, saw palmetto, nettle, red clover blossom, black cohosh, chaste tree berry, dong quai root, hop flower, licorice root, wild yam, thyme leaf, oregano, hyssop, marjoram, American ginseng, ed panax ginseng, white panax ginseng, cruciferous vegetable, schizandra, goji berry, tribulus, velvet bean, cranberry, almond, white quinoa and epimidium, wherein said grain or seed and said herbal component together make up 100% by dry weight of said growth medium, wherein said growth medium is hydrated during use with a hydrating medium.

2. The method of claim 1, wherein said growth medium includes at least one of said grain or seed together with at least one said herbal component and further wherein said hydrating medium is at least one juice.

3. The method of claim 2, wherein said grain or seed is present in about 20-25% dry weight of said growth medium, said herbal component is present in about 75-80% of the dry weight of said growth medium, said grain or seed and said herbal component add up to 100% of said growth medium, and said at least one juice is not counted in the percentage of said growth medium.

4. The method of claim 3, wherein said at least one juice is selected from the group consisting of organic carrot juice concentrate, organic concord grape juice, organic pomegranate juice concentrate, organic ginger juice, organic blueberry puree, organic acai puree, organic plum puree, organic raspberry puree, organic tomato puree, organic cranberry juice, organic goat milk, organic heavy cream, organic coconut cream, organic purple cabbage juice, organic red cabbage juice, organic beet juice, organic purple carrot juice, organic parsley juice, organic aloe vera juice, organic apple juice, organic coconut water, organic cherry juice, organic green tea, organic vegetable juice, organic pineapple juice, organic cold brewed coffee, organic almond milk, organic chicken broth, organic vegetable broth and organic roasted coffee slurry.

\* \* \* \* \*